(12) United States Patent
Grimaldi et al.

(10) Patent No.: US 8,916,142 B2
(45) Date of Patent: Dec. 23, 2014

(54) SEMI-CRYSTALLINE SUPRAMOLECULAR POLYMERS

(75) Inventors: Sandra Grimaldi, Sainte-Foy-les-Lyon (FR); Jean-Philippe Gillet, Brignais (FR); Manuel Hidalgo, Brignais (FR); Francois-Genes Tournilhac, Paris (FR); Philippe Cordier, Buros (FR); Ludwik Leibler, Paris (FR)

(73) Assignees: Arkema France, Colombes (FR); Centre National de la Recherche Scientifique (CNRS), Paris (FR)

( * ) Notice: Subject to any disclaimer, the term of this patent is extended or adjusted under 35 U.S.C. 154(b) by 1484 days.

(21) Appl. No.: 12/440,308

(22) PCT Filed: Sep. 7, 2007

(86) PCT No.: PCT/FR2007/051888
§ 371 (c)(1),
(2), (4) Date: Nov. 13, 2009

(87) PCT Pub. No.: WO2008/029065
PCT Pub. Date: Mar. 13, 2008

(65) Prior Publication Data
US 2010/0135940 A1      Jun. 3, 2010

Related U.S. Application Data

(60) Provisional application No. 60/851,610, filed on Oct. 13, 2006, provisional application No. 60/861,927, filed on Nov. 30, 2006.

(30) Foreign Application Priority Data

Sep. 8, 2006    (FR) ..................................... 06 53636
Nov. 17, 2006   (FR) ..................................... 06 54953

(51) Int. Cl.
| | | |
|---|---|---|
| *A61K 31/785* | (2006.01) | |
| *A61K 8/84* | (2006.01) | |
| *A61Q 19/00* | (2006.01) | |
| *C09D 177/00* | (2006.01) | |
| *C08G 69/00* | (2006.01) | |

(52) U.S. Cl.
CPC . *A61K 8/84* (2013.01); *A61Q 19/00* (2013.01); *A61K 2800/54* (2013.01); *C09D 177/00* (2013.01); *C08G 69/00* (2013.01)
USPC .................. 424/78.14; 424/78.08; 424/78.19; 424/78.23; 424/78.3; 424/400

(58) Field of Classification Search
None
See application file for complete search history.

(56) References Cited

U.S. PATENT DOCUMENTS

2007/0123694 A1   5/2007   Tournilhac et al.
2009/0062551 A1   3/2009   Tournilhac et al.

OTHER PUBLICATIONS

Norlin, L.H. Ulmann's Encyclopedia of industrial Chemistry, 2000, Tall oil, online article.*

* cited by examiner

*Primary Examiner* — James Rogers
(74) *Attorney, Agent, or Firm* — RatnerPrestia

(57) ABSTRACT

The invention relates to a supramolecular polymer obtained from the reaction of (i) an amine bearing a nitrogen-containing heterocyclic group: imidazolidone, trimethyleneurea or triazine, which is capable of associating by means of hydrogen bonds and (ii) at least one fatty acid monomer comprising at least one reactive function, a dimer of identical or different fatty acids and/or a trimer of identical or different fatty acids, or a derivative of said fatty acid(s) which is selected from a fatty acid ester, and a fatty acid chloride.

17 Claims, 1 Drawing Sheet

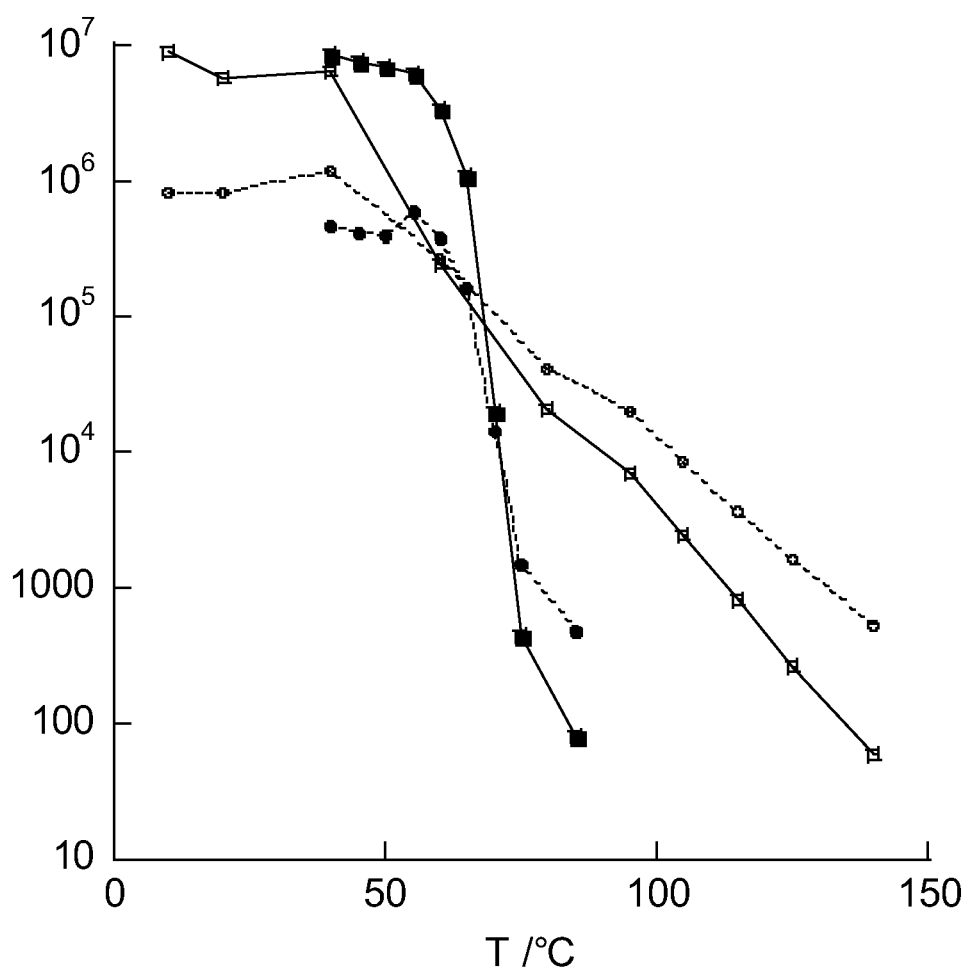

SEMI-CRYSTALLINE SUPRAMOLECULAR POLYMERS

PRIORITY CLAIM

This application claims benefit, under U.S.C. §119 or §365 of French Application Numbers FR 0653636, filed Sep. 8, 2006, and FR 0654953, filed Nov. 17, 2006; U.S. Provisional Patent Application Nos. 60/851,610 filed Oct. 13, 2006, and 60/861,927 filed Nov. 30, 2006; and PCT/FR2007/051888 filed Sep. 7, 2007.

The present invention relates to supramolecular polymers. The term "supramolecular polymers" is understood to mean polymers in which the monomers are molecules of low molecular weight ($M_n \leq 1500$) linked together by physical bonds such as, for example, hydrogen bonds, ionic bonds, hydrophobic bonds and more particularly hydrogen bonds also known as "H bridges" or "H bonds". An advantage of these supramolecular polymers is that these physical bonds are reversible, that is to say that they may easily break leading to the partial or complete depolymerization of said polymers under the influence of various factors such as temperature.

The supramolecular polymers make up, therefore, a different class of polymers than that of conventional polymers, that is to say non-supramolecular polymers, which are themselves made up of monomers linked together by covalent bonds.

There are some examples in the literature of associations between molecules that result in supramolecular polymers. Thus Patent Application EP 1 031 589 discloses the preparation of supramolecular polymers by reaction between molecules containing isocyanate functional groups or their derivatives and molecules containing hydroxy, amine or acid functional groups. Thus the reaction between isophorone diisocyanate and polytetrahydrofuran results in a supramolecular material.

Furthermore, in WO 0 107 396, the production of supramolecular polymers by reaction between an acid or an acid chloride with an aromatic derivative substituted by hydroxyl and acid functional groups, is disclosed; thus the reaction between 2,5-dihydroxybenzoic acid and dodecanoyl dichloride results in the production of a supramolecular material.

Described in Application WO 03/059964 are supramolecular materials formed by reaction, in a first step, of a fatty acid dimer with a polyamine such as diethylenetriamine (DETA), triethylenetetramine (TETA) or tetraethylenepentamine (TEPA), followed in a second step by a reaction with urea. In this Application WO 03/059964 it is recommended to take every precaution so as to prevent crystallization, especially by using mixtures of polyamines preferably having purified amines.

Described in Application WO 2006/087475 are supramolecular materials formed in a similar manner by reaction of a fatty acid dimer containing high levels of fatty acid trimer with a purified DETA or TETA, followed by a second reaction with urea. In this Application WO 2006/087475, it was shown that by proceeding in this fashion an elastomeric supramolecular material is obtained. There too recommendations are given on the possible ways of preventing crystallization that is deemed to be prejudicial to the desired properties.

The Applicant has now synthesized novel supramolecular polymers which number among their advantages, being able to be partially or completely depolymerized and this being done especially by the action of temperature, being semi-crystalline which gives them good cohesion at temperatures below the melting point of the crystalline phase and especially at room temperature, and having a low melt viscosity, useful in several fields, such as the coatings, hot melt adhesives and cosmetics fields, amongst others.

Just like the non-crystalline supramolecular materials previously described in Application WO 03/059964, the semi-crystalline supramolecular materials according to the invention exhibit a variation in mechanical properties with temperature. The difference is that in the case of the semi-crystalline materials that are the subject of the invention, the change in properties occurs in a narrow temperature range, which is an advantage in many fields of application such as that of coatings, hot-melt adhesives and powder paints.

A supramolecular polymer according to the invention is derived from the reaction between:
(i)a) a unit of formula (1) to (4)

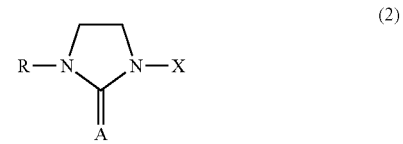

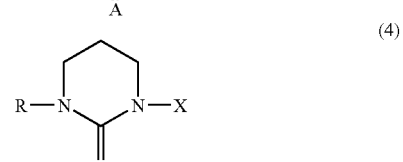

A=oxygen, sulfur or NH, preferably oxygen
X=any unit
R=unit containing a primary amine or secondary amine or alcohol functional group or
(i)b) a unit of formula (5) or (6)

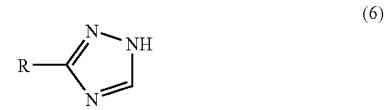

R=unit containing a primary amine or secondary amine or alcohol functional group with (ii) at least one fatty acid monomer comprising at least one reactive functional group, a dimer of identical or different fatty acids and/or a trimer of identical or different fatty acids, or a derivative of said fatty acid(s) chosen from a fatty acid ester, and a fatty acid chloride.

By way of example, the unit X may be an optionally substituted alkyl chain.

More particularly, the supramolecular polymer according to the invention is derived from the reaction between 2-aminoethyl-2-imidazolidinone (UDETA) or 3-amino-1,2,4-triazole and a mixture containing:
  51 to 100 wt % of one or more identical or different fatty acid dimers and/or one or more identical or different fatty acid trimers; and
  0 to 49 wt % of one or more identical or different fatty acid monomers and/or one or more identical or different fatty acid higher oligomers. A fatty acid higher oligomer has a molecular weight greater than the corresponding fatty acid trimer. It is a tetramer, a pentamer, etc. of said fatty acid.

The hydrogen bonds in the supramolecular polymer are made between two identical or different functional groups chosen from the functional groups of units (1) to (6). The carbon atoms in the units (1) to (6) may be substituted.

Some of the molecules containing at least one of the units (1) to (4) above correspond to the reaction of urea with a compound containing $NH_2$ or NH functional groups separated by 2 or 3 carbon atoms and more precisely to the reaction of urea with alkyleneamines, amines, aminoalcohols or amidoamines. Mention may be made, for example, of molecules comprising the units (1) which derive from the reaction of urea with a polyalkyleneamine, such as, for example:
  the molecule UDETA: 2-aminoethylimidazolidinone or 1-(2-aminoethyl)-2-imidazolidinone derived from the reaction of urea with diethylenetriamine (DETA);
  the molecule UTETA: 1-(2-[(2-aminoethyl)amino]ethyl)-2-imidazolidinone derived from the reaction of urea with triethylenetetramine (TETA); and
  the molecule UTEPA: 1-(2-{2-[(2-aminoethylamino] ethyl}amino)ethyl]-imidazolidin-2-one derived from the reaction of urea with tetraethylenepentamine (TEPA).

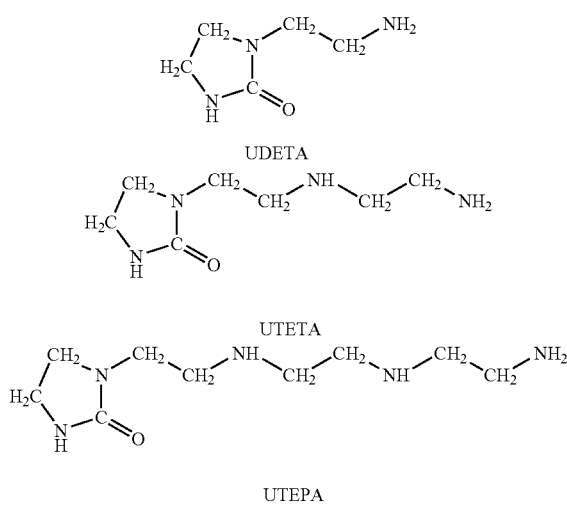

UDETA

UTETA

UTEPA

Mention may be made, as other examples of molecules comprising units (1) to (4) above, of those derived from the reaction of urea or of thiourea with:
  various polyamines such as dipropylenetriamine, di-(1,2-butylene)triamine, di-(2,3-butylene)triamine, N-methyldiethylenetriamine, N-ethyldiethylenetriamine, and tripropylenetetramine; and
  amino alcohols, such as 2-[(2-aminoethyl)amino]ethanol.

Among the molecules comprising a unit (5) above mention may be made of 4-amino-1,2,4-triazole and among the molecules comprising a unit (6) above mention may be made of 3-amino-1,2,4-triazole.

Regarding fatty acids, mention may be made of saturated or unsaturated carboxylic acids consisting of at least 5 carbon atoms such as linear monoacids, like lauric, myristic, palmitic, oleic, linoleic, stearic or linolenic acid or branched monoacids such as 2-ethylhexanoic acid, linear diacids like glutaric acid, adipic acid, pimelic acid, suberic acid, azelaic acid, sebacic acid, undecanedioic acid, dodecanedioic acid, brassylic acid, tetradecanedioic acid, pentadecanedioic acid, thapsic acid or octadecanedioic acid, or branched diacids like 3,3-dimethylglutaric acid, dimers and trimers of fatty acids of plant origin such as undecylenic, myristoleic, palmitoleic, oleic, linoleic, linolenic, ricinoleic, eicosenoic or docosenoic acid, that are found especially in pine, rapeseed, corn, sunflower, soybean, grapeseed, linseed or jojoba oils or of animal origin such as eicosapentaenoic or docosahexanoic acid that are found especially in fish oils. As preferred examples of fatty acids, mention may be made of fatty acids containing unsaturated molecules, for example of oleic type and that have been oligomerized by condensation reaction across the double bonds, thus resulting in mixtures predominantly made up of dimers and timers. The term "fatty acid dimers or trimers", is understood to mean oligomers of 2 or 3, identical or different, monomers.

Advantageously, these saturated or unsaturated fatty acids consist of 12 to 100 carbon atoms and still more advantageously between 24 and 90 carbon atoms.

The mixtures of fatty acid oligomers contain, in general, a certain amount of fatty acid dimers and trimers. The proportion of fatty acid monomer and fatty acid higher oligomers (tetramers, pentamers, etc.) is lower relative to the proportion of fatty acid dimers and fatty acids trimers. Furthermore, the fatty acid dimer/trimer ratio has a certain influence on the properties of the polymers of the invention such as the degree of crystallinity and/or the crystallization rate.

Mention may be made, as examples of a fatty acid dimer and trimer, of the following formulae that are conventionally given to represent the cyclic dimers derived from fatty acids containing 18 carbon atoms, referred to as $C_{18}$ acids, knowing that the commercially available compounds are mixtures of steric and positional isomers of these structures, optionally partially or completely hydrogenated.

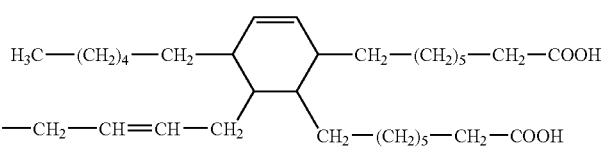

Cyclic $C_{18}$ acid dimer

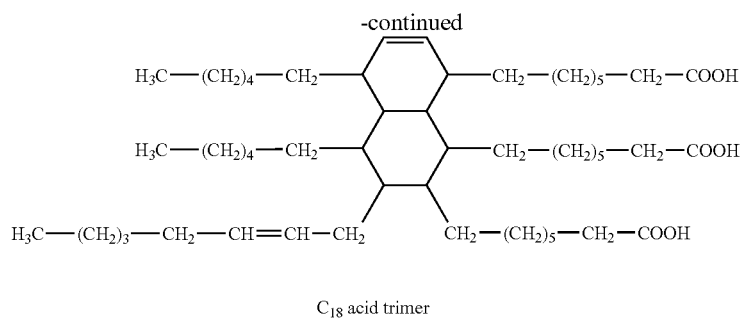

C₁₈ acid trimer

A preferred mixture of fatty acid oligomers contains dimers, trimers and monomers of linear or cyclic $C_{18}$ fatty acids, said mixture having dimers in the majority and monomers in the minority. Preferably, said mixture comprises:

0.1 to 40% by weight, preferably 0.1 to 10% by weight of identical or different fatty acid monomers;

0.1 to 99% by weight, preferably 18 to 98% by weight of identical or different fatty acid dimers; and 0.1 to 85%, preferably 2 to 70% of identical or different fatty acid trimers.

Mention may be made, as examples of fatty acid dimer/trimer mixtures, of (% by weight):

PRIPOL® 1017 from Uniqema, mixture of 75-80% dimers and 18-22% trimers with around 1-3% fatty acid monomer;

PRIPOL® 1048 from Uniqema, mixture of 50/50% dimers/trimers;

PRIPOL® 1013 from Uniqema, mixture of 95-98% dimers and 2-4% trimers with 0.2% maximum fatty acid monomer;

PRIPOL® 1006 from Uniqema, mixture of 92-98% dimers and a maximum of 4% trimers with 0.4% maximum fatty acid monomer;

UNIDYME® 60 from Arizona Chemicals, mixture of 33% dimers and 67% trimers with less than 1% fatty acid monomer;

UNIDYME® 40 from Arizona Chemicals, mixture of 65% dimers and 35% trimers with less than 1% fatty acid monomer;

UNIDYME® 14 from Arizona Chemicals, mixture of 94% dimers and less than 5% trimers and other higher oligomers with around 1% fatty acid monomer;

EMPOL® 1008 from Cognis, mixture of 92% dimers and 3% higher oligomers, predominantly trimers, with around 5% fatty acid monomer;

EMPOL® 1018 from Cognis, mixture of 81% dimers and 14% higher oligomers, predominantly trimers, with around 5% fatty acid monomer;

RADIACID® 0980 from Oleon, mixture of around 30% dimers and 70% trimers.

The products PRIPOL®, UNIDYME®, EMPOL® and RADIACID® comprise $C_{18}$ fatty acid monomers and oligomers of fatty acids corresponding to multiples of $C_{18}$.

According to one particular embodiment of the invention, the units (1) to (6) may react with a derivative of the fatty acid(s) as defined above, this fatty acid derivative been chosen from a fatty acid ester and a fatty acid chloride, to form a supramolecular polymer according to the invention.

By way of example of a fatty acid ester, mention may be made of a methyl, ethyl or isopropyl ester of a fatty acid as defined above.

One preferred fatty acid ester is a fatty acid methyl ester, and in particular a methyl ester of a fatty acid dimer or a mixture of fatty acid oligomers as defined above.

By way of example of a fatty acid chloride, mention may be made of sebacoyl chloride.

It has been possible to demonstrate the quite unique properties of these supramolecular polymers obtained after reaction (i) of molecules of formula (1) to (6) and (ii) a fatty acid, a fatty acid dimer, a fatty acid trimer or a fatty acid derivative. These supramolecular polymers are characterized by a glass transition temperature, $T_g$, most often lying below room temperature and by a melting point, $T_m$, which results in a product of viscosity <100 Pa·s at 110° C., measured, for example by a Brookfield type rheometer adapted for temperature measurements. The presence of a $T_g$ attests to a polymer-type behaviour. The presence of a $T_g$ and a $T_m$ attests to the semi-crystalline character of the material.

Mention may be made, as an example of the structure of the supramolecular polymer according to the invention, of the structure that results from the association by hydrogen bonds of molecules derived from reaction of the UDETA molecule with molecules of C18 fatty acid dimers or trimers. It can be said, as the molecules of fatty acid dimers or trimers are grafted by UDETA, that which will enable their association by hydrogen bonds derives especially from the imidazolidinone functional groups of UDETA and the amide functional groups created by the grafting.

By way of example of a semi-crystalline polymer according to the invention, mention may be made of the polymer of following formula which was obtained by reaction of a fatty acid dimer with UDETA:

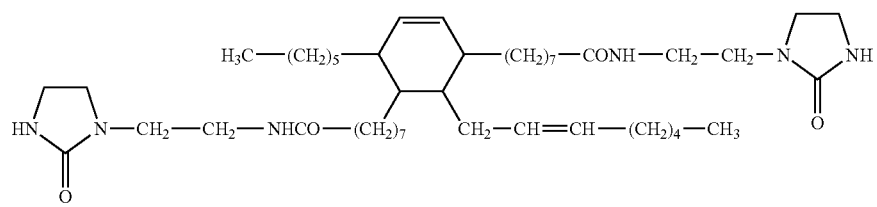

Mention may be made, as other examples of supramolecular polymers according to the invention, of UDe 1008 derived from the reaction between EMPOL® 1008 and UDETA;

UDe 1060 derived from the reaction between UNIDYME® 60 and UDETA;

UDe 1060/1008 derived from the reaction between EMPOL® 1008, UNIDYME® 60 and UDETA;

UDe 1017 derived from the reaction between PRIPOL® 1017 and UDETA;

UDe 1048 derived from the reaction between PRIPOL® 1048 and UDETA;

UDe 1014 derived from the reaction between UNIDYME® 14 and UDETA; and

UDe 0980 derived from the reaction between RADIACID® 0980 and UDETA.

Depending on the starting fatty acid, in the case of UDETA+fatty acid, a semi-crystalline polymer is obtained that has a melting point ($T_m$) most often between 30 and 150° C. and that has a glass transition temperature ($T_g$) most often between −50° C. and 20° C.

The degree of crystallinity of these semi-crystalline polymers according to the invention may be determined by X-ray diffraction at various angles of incidence, by calorimetric measurements such as DSC (Differential Scanning Calorimetry) or by any other technique enabling the proportion of the crystalline phase in the semi-crystalline polymer to be calculated.

This degree of crystallinity varies as a function of the temperature, and is higher at a temperature below the melting point ($T_m$) of the supramolecular polymer in question. It is thus possible to show by monitoring the X-ray diffraction peaks as a function of the temperature or by DSC (heat flow as a function of the temperature) how the crystallinity decreases when the temperature increases. It is also possible by using, for example, these same techniques, or even rheological techniques such as measurement of dynamic shear moduli as a function of the temperature, to demonstrate the rate of recrystallization of the semi-crystalline polymer having undergone partial or total melting of its crystalline phase. Surprisingly, it has been found that this rate might depend on the type of fatty acid used for the synthesis of the semi-crystalline supramolecular polymer. Thus, for example, it has been found that the higher the trimer content of the fatty acid used, the more slowly the system crystallized. All these properties of the semi-crystalline supramolecular polymers, i.e., the development of the crystallinity as a function of the acid used and of the temperature and the development of the crystallization rate as a function of the choice of acid (dimer/trimer proportion), enable the possibility of regulating the properties of the semi-crystalline polymer, used alone or formulated, as a function of the applications, to be envisaged.

Another variable in the synthesis of these semi-crystalline supramolecular polymers which may have an influence on the thermomechanical properties (melting point, glass transition temperature, crystallinity and dynamic moduli as a function of the temperature) is the stoichiometric ratio between the molecules (1) to (6) above, and the fatty acid molecules or fatty acid derivatives (fatty acid monomer, fatty acid dimer, fatty acid trimer, fatty acid higher oligomers, fatty acid esters, fatty acid chloride and their mixtures), having been used for their synthesis. Thus, for example, in the case of the UDETA molecule, the number of amine functional groups reactive with the acid functional groups of the fatty acid used, may be adjusted so that it lies within stoichiometric proportions, that is to say, one amine (or one molecule of UDETA) for each acid group or, else in non-stoichiometric proportions, that is to say, with a shortage or excess of amine (and therefore of UDETA) relative to the acid groups. The ratio between the number of units (1) and the number of acid groups of the monomer fatty acids, of the fatty acid dimers and/or of the fatty acid trimers is between 0.5 and 2.

It is preferable that the molar purity of the molecules of formula (1) to (6), which constitute the associative units, is as high as possible to favor the crystalline nature of the supramolecular polymer. The molar purity of the molecules used should thus be greater than 70%, and preferably greater than 85%.

The supramolecular polymer of the invention may be used alone, as it is, or in a composition comprising another polymer or a resin. One or more additives may be added to said supramolecular polymer or to said composition. They may be, for example, at least: an antioxidant, a plasticizer, a mineral filler, an organic filler, a pigment and/or a dye.

The supramolecular polymers according to the invention find applications in:

rheology and/or adhesion modifiers for coatings on various types of surface, in particular coatings that are easy to strip with a specific solvent involving hydrogen bonds;

additives to make the fluidity of paints (for example epoxy or polyester resins) vary with temperature and in particular in powder paints;

additives for modifying the gel appearance of organic solutions;

additives in the processing of thermoplastics to effect reversible crosslinking;

additives in the formulation of unmodified bitumens and modified bitumens;

additives in the formulation of cements or of building materials;

additives in the formulation of rubber;

anti-corrosion additives, in particular in protective coatings;

additives in the textile, fabric and paper field;

additives to facilitate recycling of thermoplastic substances by destruction of the hydrogen bonds by a specific solvent;

additives for impact modification in polymers, in particular in polyamides;

hot melt adhesives or "hot-melts";

solvent-based adhesives;

additives for hot melt adhesives;

additives for solvent-based adhesives;

additives for pressure-sensitive adhesives;

adhesive formulations;

additives for lubricants;

additives in cosmetic formulations;

additives in inks, and in particular in printing inks;

additives in photographic materials;

materials for printed circuits;

additives for improving the gas barrier properties of certain polymers; and additives for controlling and improving the viscosity and fluidity of formulations.

Another subject of the invention is therefore cosmetic compositions comprising a supramolecular polymer as defined above.

The cosmetic compositions that can be used in the invention may be present in all the galenic forms conventionally used for topical application and in particular in the form of an alcoholic or hydroalcoholic solution or an oily solution or a solution or a dispersion of lotion or serum type, an emulsion of liquid or semi-liquid consistency of the milk type, obtained by dispersion of a fatty phase in an aqueous phase (O/W) or vice versa (W/O), or a suspension or emulsion of soft consistency of (O/W) or (W/O) cream type, or an aqueous or anhydrous gel, an emollient, or any other cosmetic form.

The cosmetic compositions according to the invention generally comprise a physiologically acceptable medium, that is to say a medium that is compatible with cutaneous tissues such as the skin and keratin substances.

The physiologically acceptable medium is advantageously a medium that does not adversely affect the properties of increased persistence of at least one cosmetic and/or care effect, of adhesion to the keratin substances and of ease of makeup removal supplied by the composition after application.

Preferably, the physiologically acceptable medium is a medium that solubilizes the supramolecular polymers according to the invention comprising at least one solvent.

Among the solvents that can be used according to the invention, mention may be made of alcohols and preferably short alcohols, polyols, silicone oils, fluorosilicone oils, and mixtures thereof. The oils may be polar or apolar.

Among these solvents, mention may be made, by way of example, of $C_1$-$C_4$ lower alcanols such as ethanol and isopropanol, polyols, glycol ethers such as 2-butoxyethanol, ethylene glycol, glycerol, propylene glycol, diethylene glycol monoethyl ether and monomethyl ether, and also aromatic alcohols such as benzyl alcohol or phenoxyethanol and similar products or mixtures thereof.

Among the polar oils, mention may be made of hydrocarbon-based oils comprising ester, ether, acid or alcohol functional groups or mixtures thereof.

The solvents are preferably present in proportions ranging from 1 to 90% by weight, and in particular from 5 to 70% by weight relative to the total weight of the composition.

The solubility of the polymers according to the invention will be controlled by the choice of the molecules defined at (i) and (ii) above.

In a known fashion, the cosmetic composition of the invention may also contain the adjuvants customary in the cosmetic and dermatological fields insofar as the adjuvant does not impair the properties desired for the composition of the invention, such as hydrophilic or lipophilic gelling agents, hydrophilic or lipophilic active care agents, preservatives, antioxidants, fragrances, neutralizers, polymers other than those defined previously, emulsifiers and co-emulsifiers.

The composition according to the invention may be in the form of a care composition, in particular a moisturizing care composition, for keratin substances such as the skin, the lips and/or the integuments and/or in the form of a body hygiene composition especially in the form of a deodorant or makeup removing product, or in the form of a makeup product for keratin substances, and/or in the form of a cleansing product, and/or in the form of a hair product, for example a shampoo or a conditioner or else a styling product.

Advantageously, the composition contains at least one dyestuff. This dyestuff may represent from 0.01 to 50% by weight, preferably from 0.5 to 40% by weight relative to the total weight of the composition.

As dyestuffs that can be used according to the invention, mention may be made of lipophilic dyes, hydrophilic dyes, pigments and nacres customarily used in cosmetic or dermatological compositions, and mixtures thereof.

The composition of the invention may be in the form of a makeup product, in particular a colored makeup product, for the skin, in particular a foundation, optionally having care properties, a blusher, a face powder or eyeshadow, an anti-wrinkle product, an eyeliner; a makeup product for the lips such as a lipstick, optionally having care properties, a lip gloss, lip pencils; a makeup product for the integuments such as the nails, in particular a nail varnish, the eyelashes, in particular in the form of a cake mascara, the eyebrows and the hair in the form of a pencil; or a temporary tattooing product for the skin of the body.

The composition is preferably in the form of a colored product for the lips.

The composition of the invention may also be in the form of a hair dye product.

It may also be in the form of a colorless care product intended for treating the skin and in particular for moisturizing it, smoothing it, depigmenting it, nourishing it, protecting it from solar rays, or giving it a specific treatment. For this purpose it advantageously contains at least one active care agent chosen from depigmenting agents, emollients, moisturizers, anti-seborrhoeic agents, anti-acne agents, agents that promote hair regrowth, keratolytic and/or desquamating agents, anti-wrinkle and tightening agents, anti-irritants, soothing agents, vitamins, screening agents, odor absorbers and mixtures thereof.

The production of supramolecular polymers of the invention and some of their characteristics and properties will now be exemplified:

The invention is also illustrated by FIG. 1. FIG. 1 is a graphical representation of the variation in the linear viscoelastic properties of supramolecular polymers at 1 Hz under shear as a function of the temperature. The curve comprising the symbols represents the elastic modulus G' of the comparative example, the curve comprising the symbols ° represents the viscous modulus G" of the comparative example, the curve comprising the symbols ■ represents the elastic modulus G' of Example 6, the curve comprising the symbols ● represents the viscous modulus G" of the comparative example.

EXAMPLE 1

Poured into a 25 ml three-neck round-bottom flask were, 10.132 g of UNIDYME® 60 acid dimer/trimer and 5.131 g of 2-aminoethylimidazolidinone (UDETA) of greater than 95% molar purity. With a magnetic stirrer hotplate, the mixture was heated, flushed with a flow of nitrogen, at 190° C. for 24 hours. A vacuum was applied at regular intervals with a water aspirator in order to eliminate the water dissolved in the medium.

Once cooled, the reaction medium was dissolved in 150 ml of chloroform. Next the organic phase was washed four times with 200 g of a methanol/water mixture (25/75 w/w). Finally two 200 g extractions, of the same methanol/water mixture to which 10 g of a 37% concentrated hydrochloric acid aqueous solution had been added, were carried out.

The organic phase was then dried over anhydrous magnesium sulfate. The chloroform was partially evaporated under vacuum using a rotary evaporator. It was completely evaporated at 130° C. in a vacuum oven. The supramolecular polymer UDe 1060 was then obtained.

By respecting a stoichiometric ratio between the number of acid functional groups carried by the initial fatty acid mixture and the number of amine functional groups present in UDETA, a supramolecular polymer derived from UNIDYME® 60 and UDETA was obtained, characterized by a melting zone between 60 and 90° C., determined by differential scanning calorimetry with a differential heat flow calorimeter (DSC 821) from Mettler Toledo®. Below 60° C., the polymer was in solid form and above 90° C., it was completely liquid. The degree of crystallinity of the polymer at room temperature was determined by X-ray diffraction measurements to be 26%. Above the maximal temperature of the melting range, the crystallinity disappeared but there remained a certain structuration characterized by a broad X-ray diffraction peak, located around 30 Å and which may have been linked to the presence of hydrogen bonds. The polymer was also characterized by a $T_g$ of 3° C. determined by DSC.

The existence of units strongly associated by hydrogen bonding in the supramolecular polymer derived from the reaction UNIDYME® 60+UDETA was confirmed by infrared spectroscopy (see Table 1). The band at 1685 cm$^{-1}$ corresponded to the presence of an imidazolidone functional group linked by hydrogen bonding and the band at 1700 cm$^{-1}$ corresponded to the presence of a free imidazolidone functional group. In Table 1 below "yes" signifies the presence of a band and "no" signifies the absence of a band on the IR spectrograph.

TABLE 1

| Temperature (° C.) | Wavenumber (cm$^{-1}$) | |
| --- | --- | --- |
| | 1685 | 1700 |
| 70 | Yes | No |
| 80 | Yes | Yes |
| 90 | Yes | Yes |
| 130 | Yes | Yes |
| 150 | Yes | Yes |
| 190 | Yes | Yes |

EXAMPLE 2

Poured into a 25 ml three-neck round-bottom flask were, 10.265 g of EMPOL® 1008 acid dimer and 5.20 g of 2-aminoethylimidazolidinone (UDETA) of greater than 95% molar purity. With a magnetic stirrer hotplate, the mixture was heated, flushed with a flow of nitrogen, at 190° C. for 24 hours. A vacuum was applied at regular intervals with a water aspirator in order to eliminate the water dissolved in the medium.

Once cooled, the reaction medium was dissolved in 150 ml of chloroform. Next the organic phase was washed four times with 200 g of a methanol/water mixture (25/75 w/w). Finally two 200 g extractions, of the same methanol/water mixture to which 10 g of a 37% concentrated hydrochloric acid aqueous solution had been added, were carried out.

The organic phase was then dried over anhydrous magnesium sulfate. The chloroform was partially evaporated under vacuum using a rotary evaporator. It was completely evaporated at 130° C. in a vacuum oven. The supramolecular polymer UDe 1008 was then obtained.

The degree of crystallinity measured by X-ray diffraction was 48% at room temperature.

EXAMPLE 3

Poured into a 25 ml three-neck round-bottom flask were, 10.25 g of a mixture of Unidyme® 60/EMPOL® 1008 (70/30 w/w) acid dimers and 5.192 g of 2-aminoethylimidazolidinone (UDETA) of greater than 95% molar purity. With a magnetic stirrer hotplate, the mixture was heated, flushed with a flow of nitrogen, at 190° C. for 24 hours. A vacuum was applied at regular intervals with a water aspirator in order to eliminate the water dissolved in the medium.

Once cooled, the reaction medium was dissolved in 150 ml of chloroform. Next the organic phase was washed four times with 200 g of a methanol/water mixture (25/75 w/w). Finally two 200 g extractions, of the same methanol/water mixture to which 10 g of a 37% concentrated hydrochloric acid aqueous solution had been added, were carried out.

The organic phase was then dried over anhydrous magnesium sulfate. The chloroform was partially evaporated under vacuum using a rotary evaporator. It was completely evaporated at 130° C. in a vacuum oven. The supramolecular polymer UDe 1060/1008 was then obtained.

EXAMPLE 4

Poured into a 25 ml three-neck round-bottom flask were, 9.875 g of UNIDYME® 14 acid dimer and 5.001 g of 2-aminoethylimidazolidinone (UDETA) of greater than 95% molar purity. With a magnetic stirrer hotplate, the mixture was heated, flushed with a flow of nitrogen, at 190° C. for 24 hour. A vacuum was applied at regular intervals with a water aspirator in order to eliminate the water dissolved in the medium.

Once cooled, the reaction medium was dissolved in 150 ml of chloroform. Next the organic phase was washed four times with 200 g of a methanol/water mixture (25/75 w/w). Finally two 200 g extractions, of the same methanol/water mixture to which 10 g of a 37% concentrated hydrochloric acid aqueous solution had been added, were carried out.

The organic phase was then dried over anhydrous magnesium sulfate. The chloroform was partially evaporated under vacuum using a rotary evaporator. It was completely evaporated at 130° C. in a vacuum oven. The supramolecular polymer UDe 1014 was then obtained.

EXAMPLE 5

Introduced into a glass reactor equipped with a variable speed stirrer motor, with inlets for introducing reactants, for introducing inert gases, such as nitrogen, and for measurement probes (e.g., temperature probe), with a vapour condensation/extraction system which could be connected to a vacuum-producing system (vacuum pump, vacuum traps, etc.), and a jacket enabling the contents of the reactor to be heated/cooled by circulating inside it a heat-transfer fluid, such as oil, coming from a thermostated bath, were 100 g of UNIDYME® 60 acid dimer/trimer of 189.4 acid number (mg KOH/g of product necessary to neutralize the acid groups), and the mixture was heated to 60-80° C. with stirring. Then 56.6 g of 2-aminoethylimidazolidinone (UDETA) of around 88% molar purity, which had been preheated (to around 60° C.) were slowly introduced, and homogenized by stirring. The reaction medium was then brought to 160° C. so as to bring about the amine (of UDETA)-acid (of fatty acid dimer/trimer mixture) reaction while extracting the condensation water, especially by flushing the top of the reactor with nitrogen. The reaction was left to proceed for 7 hours, after which the reaction medium was cooled. The supramolecular polymer UDe 1060a was then obtained. The solidification point of the product was located at 92° C. and the residual acid number obtained was 7.46. The $T_g$ of the polymer determined using a DSC Q10 machine from TA Instruments was −1° C. and the melting range of the whole crystalline phase went from 56° C. (start of the peak) to 90° C. (end of the peak).

EXAMPLE 6

Introduced into a glass reactor such as described in Example 5 were, 145 g of PRIPOL® 1017 acid dimer/trimer, of 193.4 acid number (mg KOH/g of product necessary to neutralize the acid groups), and the mixture was heated to 60-80° C. with stirring. Then 161 g of 2-aminoethylimidazolidinone (UDETA) of around 88% molar purity which had been preheated (to around 60° C.) were slowly introduced, and homogenized by stirring. The reaction medium was then brought to 160° C. so as to bring about the amine (of UDETA)-acid (of fatty acid dimer/trimer mixture) reaction while extracting the condensation water, especially by flushing the top of the reactor with nitrogen. The reaction was left to proceed for 16 hours, after which the reaction medium was cooled. The supramolecular polymer UDe 1017 excess UDETA was then obtained. The solidification point of the product was located at 61° C. and the residual acid number obtained was 1.49. The polymer was also characterized by a $T_g$ of −15 to 10° C., determined using a DSC Q10 machine from TA Instruments. With this same DSC machine the melting range of the crystalline phase was discovered between 40 and 85° C. When the sample was melted at a temperature above 85° C. and cooled rapidly (10° C./rain), the crystallization did not occur, so that the DSC, after such a treatment, only showed the $T_g$ at −15 to −10° C. and the absence of any melting up to 100° C. It suffices, then, to leave the sample for a certain time at a temperature below that of the melting range, for example, one hour at 40° C. in order to rediscover a melting peak during a DSC experiment. The shape of the melting peak and the intensity of the melting (represented by the melting energy) depend on the time and on the temperature at which the sample has been left before carrying out the DSC measurement. This shows that crystallization of the crystalline phase of the semi-crystalline supramolecular polymer is not immediate and that the crystallization rate depends on the time and the temperature.

In the infrared spectrum at ambient temperature, two different bands were detected for the $vC=O$ stretching vibration of the amide group, the wave numbers of which are located at 1654 cm$^{-1}$ and 1641 cm$^{-1}$. As the temperature rises, the disappearance of the crystalline phase is accompanied by a decrease in the absorbance at 1641 cm$^{-1}$ (Table 2). This shows that the band at 1654 cm$^{-1}$ corresponds to the $vC=O$ vibration of the amide group in the amorphous state whereas the band at 1641 cm$^{-1}$ corresponds to the $vC=O$ vibration of the amide group in the crystalline state.

TABLE 2

| Temperature | Absorbance at 1654 cm$^{-1}$ | Absorbance at 1641 cm$^{-1}$ |
|---|---|---|
| 45 | 0.475 | 0.473 |
| 50 | 0.476 | 0.462 |
| 55 | 0.482 | 0.448 |
| 60 | 0.487 | 0.428 |
| 65 | 0.492 | 0.406 |
| 70 | 0498 | 0.386 |
| 75 | 0.500 | 0.364 |

EXAMPLE 7

Introduced into a glass reactor such as described in Example 5 were 150.5 g of PRIPOL® 1048 acid dimer/trimer, of 187.3 acid number (mg KOH/g of product necessary to neutralize the acid groups) and the mixture was heated to 60-80° C. with stirring. Then 161 g of 2-aminoethylimidazolidinone (UDETA) of around 88% molar purity, which had been preheated (to around 60° C.) were slowly introduced and homogenized by stirring. The reaction medium was then brought to 160° C. so as to bring about the amine (of UDETA)-acid (of fatty acid dimer/trimer mixture) reaction while extracting the condensation water, especially by flushing the top of the reactor with nitrogen. The reaction was left to proceed for 16 hours, after which the reaction medium was cooled. The supramolecular polymer UDe 1048 excess UDETA was then obtained. The solidification point of the product was located at 71° C. and the residual acid number obtained was 3.1. The polymer was also characterized by a $T_g$ of around −29° C., determined using a DSC Q10 machine from TA Instruments. With this same DSC machine, the melting range of the crystalline phase was discovered between 40 and 85° C. Observation of the crystallization of a molten sample left at room temperature clearly showed a difference from the supramolecular polymer of Example 6. In fact, the supramolecular polymer UDe 1048 excess UDETA crystallized more slowly than the supramolecular polymer UDe 1017 excess UDETA. Rheology experiments (measurements of the dynamic shear moduli as a function of the time) were carried out comparatively with the supramolecular polymers UDe 1017 excess UDETA and UDe 1048 excess UDETA, preheated to melt the crystalline phase, using an ARES rheometer of parallel plate geometry with a gap of 20 mm, an applied stress of 100 Pa at 40° C. and a frequency of 0.1 Hz. While the sample of polymer UDe 1017 excess UDETA climbed in cohesion (increase of dynamic moduli and especially of the storage modulus G') to reach a near plateau at the end of 2000 s with a G' value slightly below $10^7$ Pa, the sample of polymer UDe 1048 excess UDETA climbed more slowly in cohesion and took around 200 000 s to reach similar G' values. The rise in cohesion at 40° C. could only be linked to the crystallization of the system, these experiments showed that the crystallization rate was much faster with the polymer UDe 1017 excess UDETA (20% timer) than with the polymer UDe 1048 excess UDETA (50/50 dimer/trimer).

EXAMPLE 8

Introduced into a 3 liter glass reactor fitted with a mechanical stirrer, a temperature probe, a nitrogen inlet via a dip tube, a dropping funnel, a condenser leading to a receiving flask and a heating mantle, were 1488 g of PRIPOL® 1017 (acid number=193 mg of KOH/g, or 5.12 mol of acid functional groups). Into the dropping funnel, 701 g of 2-aminoethylimidazolinone (UDETA, molar purity around 88%, alkalinity index=7.3 meq/g or 5.12 mol, 1 equivalent) were introduced in the molten state. The reactor was heated to 80° C., then with stirring and under a flow of nitrogen, the UDETA was added dropwise over a period of 30 minutes. The temperature was raised progressively to 180° C. over a period of 4 hours, then it was left to react for 4 hours at 180° C. The quantity of water recovered was 73 g (4.1 mol). The reactor was left to cool to 100° C. in order to recover 1971 g of a viscous brown liquid that solidified at room temperature, the supramolecular polymer UDe 1017 stoichiometric. The residual acid number of the product was 6 mg KOH per g and the residual alkalinity index of the product was 0.2 milliequivalents/g. The polymer was also characterized by a $T_g$ of around −13° C., determined using a DSC Q10 machine from TA Instruments. With this same DSC machine, the melting range of the crystalline phase was discovered between 40 and 85° C. The heat softening temperature of the product was also determined using an NBA 440 ring-and-ball apparatus from Normalab Analis. Thus a ring-and-ball softening point was discovered at 81° C.

EXAMPLE 9

Introduced into a 3 liter glass reactor fitted with a mechanical stirrer, a temperature probe, a nitrogen inlet via a dip tube, a dropping funnel, a condenser leading to a receiving flask and a heating mantle, were 1688 g of PRIPOL® 1048 (acid number=187 mg of KOH/g, or 5.63 mol of acid functional groups). Into the dropping funnel, 811 g of 2-aminoethylimidazolinone (UDETA, molar purity around 88%, alkalinity index=7.3 meq/g or 5.92 mol, 1.05 equivalents) were introduced in the molten state. The reactor was heated to 80° C., then with stirring and under a flow of nitrogen, the UDETA was added dropwise over a period of 30 minutes. The temperature was raised progressively to 180° C. over a period of 4 hours, then it was left to react for 4 hours at 180° C. The quantity of water recovered was 90 g (5 mol). The reactor was left to cool to 100° C. in order to recover 2266 g of a viscous brown liquid that solidified at room temperature, the supramolecular polymer UDe 1048 stoichiometric. The residual acid number of the product was 5 mg KOH per g and the residual alkalinity index of the product was 0.2 milliequivalents/g. The polymer was also characterized by a $T_g$ of around −4° C., determined using a DSC Q10 machine from TA Instruments. With this same DSC machine, the melting range of the crystalline phase was discovered between 40 and 85° C. The heat softening temperature of the product was also determined using an NBA 440 ring-and-ball apparatus from Normalab Analis. Thus a ring-and-ball softening point was discovered at 82.9° C.

EXAMPLE 10

Introduced into a 3 liter glass reactor fitted with a mechanical stirrer, a temperature probe, a nitrogen inlet via a dip tube, a dropping funnel, a condenser leading to a receiving flask and a heating mantle, were 1125 g of RADIACID® 0980 (acid number=184 mg of KOH/g, or 3.69 mol of acid functional groups). Into the dropping funnel, 536 g of 2-aminoethylimidazolinone (UDETA, molar purity around 88%, alkalinity index=7.3 meq/g or 3.91 mol, 1.05 equivalents) were introduced in the molten state. The reactor was heated to 80° C., then with stirring and under a flow of nitrogen, the UDETA was added dropwise over a period of 30 minutes. The temperature was raised progressively to 180° C. over a period of 5 hours, then it was left to react for 3 hours at 180° C. The quantity of water recovered was 57 g (3.2 mol). The reactor was left to cool to 100° C. in order to recover 1500 g of a viscous brown liquid that solidified at room temperature, the supramolecular polymer UDe 980 stoichiometric. The residual acid number of the product was 7 mg KOH per g and the residual alkalinity index of the product was 0.2 milliequivalents/g. The polymer was also characterized by a $T_g$ of around −21° C., determined using a DSC Q10 machine from TA Instruments. With this same DSC machine, the melting range of the crystalline phase was discovered between 40 and 75° C. The heat softening temperature of the product was also determined using an NBA 440 ring-and-ball apparatus from Normalab Analis. Thus a ring-and-ball softening point was discovered at 82° C.

EXAMPLE 11

Introduced into a 3 liter glass reactor fitted with a mechanical stirrer, a temperature probe, a nitrogen inlet via a dip tube, a dropping funnel, a condenser leading to a receiving flask and a heating mantle, were 1203 g of RADIACID® 0980 (acid number=184 mg of KOH/g, or 3.94 mol of acid functional groups). Into the dropping funnel, 406 g of 2-aminoethylimidazolinone (UDETA, molar purity around 88%, alkalinity index=7.3 meq/g or 2.96 mol, 0.75 equivalents) were introduced in the molten state. The reactor was heated to 80° C., then with stirring and under a flow of nitrogen, the UDETA was added dropwise over a period of 30 minutes. The temperature was raised progressively to 180° C. over a period of 5 hours, then it was left to react for 3 hours at 180° C. The quantity of water recovered was 46 g (2.6 mol). The reactor was left to cool to 100° C. in order to recover 1446 g of a viscous brown liquid that solidified at room temperature, the supramolecular polymer UDe 980 shortage of UDETA. The residual acid number of the product was 31 mg KOH per g and the residual alkalinity index of the product was 0.05 milliequivalents/g. The polymer was also characterized by a $T_g$ of around −20° C., determined using a DSC Q10 machine from TA Instruments. With this same DSC machine, the melting range of the crystalline phase was discovered between 40 and 60° C. The heat softening temperature of the product was also determined using an NBA 440 ring-and-ball apparatus from Normalab Analis. Thus a ring-and-ball softening point was discovered at 43° C. It was also noticed by observation of the appearance of the samples that the polymer UDe 980 shortage of UDETA crystallized much more slowly than the polymer UDe 980 stoichiometric. In fact, the sample UDe 980 shortage of UDETA kept a transparent appearance for much longer.

EXAMPLE 12

Placed in a 100 ml round-bottomed flask equipped with a magnetic stirrer and an oil bath heating system were 4.04 g of sebacic acid (20.0 mmol) and 2.58 g of UDETA (20.0 mmol). The mixture was kept at 170° C. for twelve hours at ambient pressure, then one hour under vacuum at the same temperature. The liquid obtained was poured into a Teflon mold. After cooling, a solid object in the shape of the mold was obtained. Differential scanning calorimetry analysis carried out on a DSC-TGA machine from TA Instruments and the polarized light microscopy observations made with a DMRD microscope from Leitz equipped with a Fluotar 10× lens and a Mettler FP80 hot stage show that it is a semi-crystalline material having a melting point of 120-125° C.

EXAMPLE 13

Placed in a 250 ml round-bottomed flask equipped with a magnetic stirrer, an oil bath heating system, a solid/liquid Soxhlet type extractor and a water condenser were 3.97 g (14 mmol) of Empol® 1016 acid dimer, 8 ml of methanol, 60 ml of chloroform and 1 ml of sulfuric acid. The thimble of the extractor was filled with 18 g of anhydrous magnesium sulfate. The mixture was placed under reflux for 24 hours, the analysis by infrared spectroscopy showed the disappearance of the acid C=O band at 1711 $cm^{-1}$ and the presence of an ester C=O band at 1742 $cm^{-1}$. The reaction mixture was washed with water and after settling the organic phase was separated, dried over anhydrous magnesium sulfate and evaporated to dryness. Thus 3.65 g (12 mmol) of fatty acid ester were obtained.

EXAMPLE 14

Placed in a 100 ml round-bottomed flask equipped with a magnetic stirrer and an oil bath heating system were 550 mg of UDETA (4.3 mmol) and 600 mg of fatty acid ester (2.0 mmol) prepared according to Example 13. The mixture was brought to 140° C. with stirring for one hour. The analysis by infrared spectroscopy showed the disappearance of the ester C=O signal at 1742 $cm^{-1}$ and the appearance of imidazolidone and amide C=O signals at 1694 and 1652 $cm^{-1}$. The reaction mixture was degassed under vacuum, cooled, put into solution in chloroform and washed twice with water. After settling, the organic phase was separated, dried over anhydrous magnesium sulfate and evaporated to dryness. The product obtained was analysed by DSC (DSC Q1000 from TA Instruments) showing the existence of a semi-crystalline structure with a glass transition at −11° C. and melting point at 70° C. The viscoelastic analysis at 0.1 Hz (ARES from Rheometrics) revealed the following values (Table 3):

TABLE 3

| Temperature (° C.) | Elastic modulus (MPa) | Viscous modulous (MPa) |
|---|---|---|
| 30 | 17.5 | 2.1 |
| 40 | 7.0 | 1.7 |
| 50 | 3.5 | 1.0 |
| 60 | 1.0 | 0.28 |
| 70 | 0.07 | 0.025 |
| 80 | <0.0004 | 0.0007 |

EXAMPLE 15

COMPARATIVE

Non-crystalline supramolecular polymer according to WO 03/059964:

Placed in a 500 ml round-bottomed flask equipped with a magnetic stirrer and a condenser were 47 g of Crayamid 115 and 16 g of urea. Crayamid 115 is a polyamide (molecular weight ~2000-4000 g/mol), the condensation product of a TOFA type acid dimer and triethylene tetramine. It contains around 26% by weight of unreacted triethylene tetramine.

The flask was immersed in an oil bath at 100° C. The temperature of the bath was gradually raised (approximately +20° C./hour). The use of pH indicator paper at the top of the condenser made it possible to check the release of ammonia. When the temperature reached 180° C., stirring became difficult. After reacting for at least 2 h at 180° C., the heating was turned off. At the end of the reaction an excess of urea may be sublimed and condensed on the walls of the flask.

After cooling, the possible excess of urea was eliminated with water by rapid rinsing of the walls of the flask. The reaction mixture of glassy appearance was dissolved in 300 ml of chloroform, dried over magnesium sulfate, then filtered through 4 g of silica gel. The solution obtained was evaporated to dryness at 60° C. under vacuum for analysis:

In the infrared IR spectrum, the vC═O vibrational band of the amide group was detected at 1654 cm$^{-1}$, indicating a non-crystalline state.

The differential scanning calorimetry analysis carried out on a DSC Q1000 machine from TA Instruments demonstrated as a single phase transition, the glass transition at 49° C.

The difference in behavior between the non-crystalline supramolecular polymer (according to WO 03/059964) and the semi-crystalline supramolecular polymer according to the invention is visible in the linear viscoelastic properties at 1 Hz (cone/plate 20 mm) (FIG. 1).

Indeed, it is observed in FIG. 1 that only the semi-crystalline materials that are the subject of the invention make it possible to obtain a large variation in the mechanical properties over a narrow temperature range.

The invention claimed is:

1. A supramolecular polymer derived from the reaction between (i)a) a unit of formula (1) to (4)

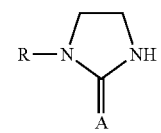

(1)

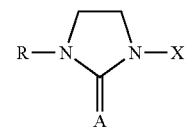

(2)

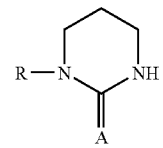

(3)

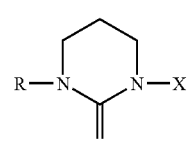

(4)

A=oxygen, sulfur or NH,
X=an optionally substituted alkyl chain,
R=a unit containing a primary amine or secondary amine or alcohol functional group or (i)b) a unit of formula (5) or (6)

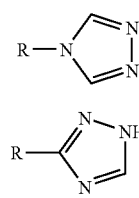

(5)

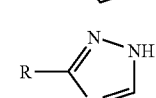

(6)

R=a unit containing a primary amine or secondary amine or alcohol functional group with
(ii) a mixture comprising:
(a) 0.1 to 40% by weight of at least one fatty acid monomer comprising at least one reactive functional group or a derivative of said fatty acid monomer(s) chosen from a fatty acid ester and a fatty acid chloride,
(b) 0.1 to 99% by weight of a dimer of identical or different fatty acids, or a derivative of said fatty acid dimer chosen from a fatty acid ester and a fatty acid chloride, and
(c) 0.1 to 85% by weight of a trimer of identical or different fatty acids, or a derivative of said fatty acid trimer chosen from a fatty acid ester and a fatty acid chloride,
wherein the supramolecular polymer is semi-crystalline.

2. The polymer as claimed in claim 1, wherein the fatty acid monomer, the dimer fatty acids and the trimer fatty acids are chosen from saturated or unsaturated fatty acids consisting of 12 to 100 carbon atoms.

3. The polymer as claimed in claim 1, wherein the fatty acid(s) are selected from the group consisting of glutaric acid, adipic acid, pimelic acid, suberic acid, azelaic acid, sebacic acid, 3,3-dimethylglutaric acid, undecanedioic acid, dodecanedioic acid, brassylic acid, tetradecanedioic acid, pentadecanedioic acid, thapsic acid, octadecanedioic acid, lauric acid, myristic acid, palmitic acid, oleic acid, linoleic acid, stearic acid, and linolenic acid.

4. The polymer as claimed in claim 1, wherein the fatty acid or acids are identical or different fatty acid dimers and trimers selected from the group consisting of undecylenic, myristoleic, palmitoleic, oleic, linoleic, linolenic, ricinoleic, eicosenoic, docosenoic, eicosapentaenoic and docosahexaenoic acid.

5. The polymer as claimed in claim 1, wherein the molecule containing at least one unit (1) is chosen from 1-(2-aminoethyl)-2-imidazolidinone (UDETA), 1-(2-[(2-aminoethyl)amino]ethyl)-2-imidazolidinone (UTETA) and 1-(2-{2-[(2-aminoethylamino]ethyl}amino)ethyl]-imidazolidin-2-one (UTEPA).

6. The polymer as claimed in claim 1, wherein the ratio between the number of units (1) to (6) and the number of acid groups of the monomer fatty acids, of the fatty acid dimers and of the fatty acid trimers is between 0.5 and 2.

7. The polymer as claimed in claim 1, wherein its melting point ($T_m$) is between 30 and 150° C.

8. The polymer as claimed in claim 1, wherein its glass transition temperature ($T_g$) is between −50° C. and 20° C.

9. A composition comprising a supramolecular polymer derived from the reaction between (i)a) a unit of formula (1) to (4)

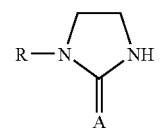

(1)

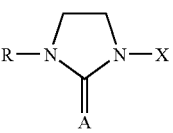

(2)

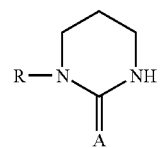

(3)

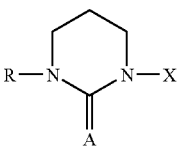

(4)

A=oxygen, sulfur or NH,
X=an optionally substituted alkyl chain,
R=a unit containing a primary amine or secondary amine or alcohol functional group or (i) b) a unit of formula (5) or (6)

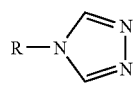

(5)

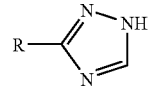

(6)

R=a unit containing a primary amine or secondary amine or alcohol functional group with
(ii) a mixture comprising:
(a) 0.1 to 40% by weight of at least one fatty acid monomer comprising at least one reactive functional group or a derivative of said fatty acid monomer(s) chosen from a fatty acid ester and a fatty acid chloride,
(b) 0.1 to 99% by weight of a dimer of identical or different fatty acids, or a derivative of said fatty acid dimer chosen from a fatty acid ester and a fatty acid chloride, and
(c) 0.1 to 85% by weight of a trimer of identical or different fatty acids, or a derivative of said fatty acid trimer chosen from a fatty acid ester and a fatty acid chloride,
wherein the supramolecular polymer is semi-crystalline.

10. The composition as claimed in claim 9, comprising at least one additive selected from the group consisting of a plasticizer, a mineral filler, an organic filler, a pigment and a dye.

11. The composition as claimed in claim 9, comprising a cosmetic composition which further comprises at least one solvent selected from water, alcohols, polyols, hydrocarbon-based oils, silicone oils, fluorosilicone oils, and mixtures thereof.

12. The composition as claimed in claim 10, comprising at least one adjuvant chosen from hydrophilic or lipophilic gelling agents, hydrophilic or lipophilic active agents, preservatives, antioxidants, solvents, fragrances, hydrophilic screening agents, odor absorbers, neutralizers, and emulsifiers.

13. The composition as claimed in claim 12, wherein the active agents are chosen from depigmenting agents, emollients, moisturizers, anti-seborrhoeic agents, anti-acne agents, agents that promote hair regrowth, keratolytic and/or desquamating agents, anti-wrinkle and tightening agents, anti-irritants, soothing agents, vitamins, screening agents, odor absorbers and mixtures thereof.

14. The composition as claimed in claim 9, comprising at least one dyestuff chosen from lipophilic dyes, hydrophilic dyes, pigments, nacres and mixtures thereof.

15. The polymer composition as claimed in claim 9, wherein the polymer composition is an additive in one or more of the following: a coating; an epoxy or polyester paint; a hot-melt or solvent-based adhesive; a lubricant; an adhesive formulation; an ink; a photographic material; an unmodified bitumen; a modified bitumen; a cement or building material; or a rubber formulation.

16. The polymer as claimed in claim 2, wherein said fatty acid monomer, dimer fatty acids and trimer fatty acids are chosen from saturated or unsaturated fatty acids consisting of 24 to 90 carbon atoms.

17. The polymer as claimed in claim 1, wherein said mixture comprises:
a. 0.1 to 10% by weight of identical or different fatty acid monomers;
b. 18 to 98% by weight of identical or different fatty acid dimers; and
c. 2 to 70% of identical or different fatty acid trimers.

* * * * *